United States Patent [19]

Copp et al.

[11] Patent Number: 4,572,913

[45] Date of Patent: Feb. 25, 1986

[54] USE OF 3-(ARYLMETHYLENEAMINO)-1-ARYL-2-PYRAZOLINES IN THE PROPHYLAXIS AND TREATMENT OF INFLAMMATION, PAIN, PYRESIS, AND ASTHMA

[75] Inventors: Frederick C. Copp, Beckenham; Albert G. Caldwell, West Wickham; David Collard, Beckenham, all of England

[73] Assignee: Burroughs Wellcome Co., Research Triangle Park, N.C.

[21] Appl. No.: 331,009

[22] Filed: Dec. 15, 1981

[30] Foreign Application Priority Data

Dec. 23, 1980 [GB] United Kingdom ............... 8041149
Mar. 18, 1981 [GB] United Kingdom ............... 8108478

[51] Int. Cl.⁴ .................. A61K 31/415; A61K 31/44; A61K 31/47; C07D 231/06
[52] U.S. Cl. .................................... 514/403; 514/313; 514/314; 514/333; 514/341; 548/379
[58] Field of Search ............ 542/414, 422, 424; 424/258, 263, 266, 273 P; 514/313, 314, 333, 341, 407; 548/379

[56] References Cited

PUBLICATIONS

Duffin et al., J. Chem. Soc. 1954, pp. 408–415.
Kost et al., Fhur. Obshchei Khim. 29, pp. 498–502 (1959), [Translation and Abstract].

*Primary Examiner*—Richard A. Schwartz
*Assistant Examiner*—Kurt G. Briscoe
*Attorney, Agent, or Firm*—Donald Brown

[57] ABSTRACT

Compounds of formula (I)

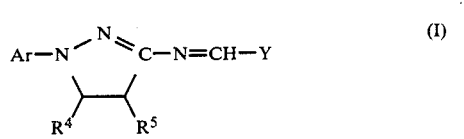

inhibit both the cyclo-oxygenase and lipoxygenase pathways of arachidonic acid oxygenation and are useful in medicine as, e.g., anti-inflammatory and anti-asthmatic agents.

The compounds may be administered as the raw chemical or in association with a carrier as a pharmaceutical formulation.

The compounds may be prepared by methods analogous to those known in the art, e.g., by the method of Duffin and Kendall in J. Chem. Soc. (1954), 408–415, or by other methods.

17 Claims, No Drawings

USE OF 3-(ARYLMETHYLENEAMINO)-1-ARYL-2-PYRAZOLINES IN THE PROPHYLAXIS AND TREATMENT OF INFLAMMATION, PAIN, PYRESIS, AND ASTHMA

This invention relates to heterocyclic compounds and their preparation and to the use of such compounds of pharmaceutical formulations thereof in medicine in a mammal, including man, as e.g. anti-inflammatory or anti-allergic agents or as agents in the prevention of tissue rejection.

Accordingly, the present invention relates to heterocyclic compounds of formula (I) and salts thereof:

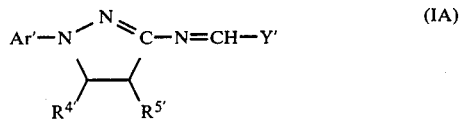
(I)

wherein, Y is a monocyclic or bicyclic aromatic radical having from 5 to 10 ring atoms selected from carbon and nitrogen optionally substituted in any position of the ring by one or more substituent(s); $R^4$ and $R^5$ are each the same or different and are each selected from hydrogen, alkyl or Y as defined above; Ar is selected from Y as defined above with the proviso that Ar is other than unsubstituted phenyl.

Examples of Ar include substituted-phenyl, naphthyl, quinolyl and pyridyl. Particularly preferred aromatic radicals are substituted-phenyl and pyridyl, especially wherein 'pyridyl' is selected from 2-pyridyl and 4-pyridyl.

The aromatic ring is preferably substituted and examples of suitable substituents are halo, alkyl (which may itself be optionally substituted by halo), carboxy, alkoxy, nitro, amino (which may itself be optionally substituted by 1 or 2 alkyl groups), hydroxy and alkyl-sulphonyl of which the alkyl moiety may itself be optionally substituted by halo. Examples of especially suitable Ar substituents are halo (that is: fluoro, chloro, bromo and iodo) and trifluoromethyl. When Ar is substituted-phenyl, the preferred positions of the ring for the substituent(s) are those selected from the 2-, 3-, 4-, 3,4- and 2,6-positions. For example, Ar may be selected from 3-trifluoromethylphenyl, 4-trifluoromethylphenyl, 4-fluorophenyl, 4-chlorophenyl, 4-bromophenyl, 3-trifluoromethyl-4-fluorophenyl, 3-trifluoromethyl-4-chlorophenyl and 3-trifluoromethyl-4-bromophenyl. When Ar is pyridyl, the preferred position of the ring for any substituent is the 5-position. For example, Ar may be selected from 5-chloro-2-pyridyl, 5-bromo-2-pyridyl and 5-iodo-2-pyridyl.

When any of $R^4$ and $R^5$ are Y the aromatic ring is preferably unsubstituted. For example, $R^4$ and $R^5$ may be selected from phenyl, 2-pyridyl and 4-pyridyl, but are preferably selected from hydrogen and alkyl.

Y is preferably a monocyclic aromatic radical having either from 3 to 7 ring atoms selected from carbon and nitrogen or a monocyclic or bicyclic aromatic radical of from 5 to 10 carbon atoms. Examples of such aromatic radicals are phenyl, pyridyl, naphthyl and pyrrolyl. When Y is substituted in the aromatic ring, the substituents may be selected from those examples described hereinbefore in the definition of 'Ar'. The preferred positions of the ring for any substituent are those selected from the 2-, 2,4- and 2,6-positions. For example, Y may be selected from 2-hydroxyphenyl and 2,4-dihydroxyphenyl.

A subclass of the compounds of formula (I) are compounds of formula (IA)

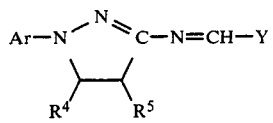
(IA)

wherein

Y' is phenyl, pyridyl, pyrrolyl, naphthyl or quinolyl, each of which may optionally be substituted by one or more of halo, alkyl, alkoxy and hydroxy groups;

$R^{4'}$ and $R^{5'}$ are the same or different and are selected from hydrogen and alkyl; and Ar' is pyridyl, quinolyl or substituted-phenyl, each of which pyridyl and quinolyl may be optionally substituted by one or more substituents, and the substituents are selected from halo, alkyl (which may itself be optionally substituted by halo), alkoxy and carboxyl groups.

Examples of compounds of formula (I) are:
3-salicylideneamino-1-(3-trifluoromethylphenyl)-2-pyrazoline;
3-benzylideneamino-1-(3-trifluoromethylphenyl)-2-pyrazoline;
3-(2,4-dihydroxybenzylideneamino)-1-(3-trifluoromethylphenyl)-2-pyrazoline;
3-(2-pyridylmethyleneamino)-1-(3-trifluoromethylphenyl)-2-pyrazoline;
3-(2-pyrrolylmethyleneamino)-1-(3-trifluoromethylphenyl)-2-pyrazoline;
3-salicylideneamino-1-(2-pyridyl)-2-pyrazoline;
3-(3-quinolylmethyleneamino)-1-(3-trifluoromethylphenyl)-2-pyrazoline;
3-(1-naphthylmethyleneamino)-1-(3-trifluoromethylphenyl)-2-pyrazoline;
3-(4-methylbenzylideneamino)-1-(2-naphthyl)-2-pyrazoline;
3-salicylideneamino-1-(3-quinolyl)-2-pyrazoline;
3-(4-chlorobenzylideneamino)-1-(4-chlorophenyl)-2-pyrazoline;
1-(4-bromo-3-trifluoromethylphenyl)-3-(2-hydroxybenzylideneamino)-2-pyrazoline;
1-(4-bromo-3-trifluoromethylphenyl)-3-(4-methoxybenzylideneamino)-2-pyrazoline;
3-benzylideneamino-1-(3-t-butylphenyl)-2-pyrazoline;
3-benzylideneamino-1-(3-trifluoromethylphenyl)-2-pyrazoline;
1-(5-bromo-6-methyl-2-pyridyl)-3-salicylideneamino-2-pyrazoline;
1-(5-bromo-6-methyl-2-pyridyl)-3-(1-naphthylmethyleneamino)-2-pyrazoline;
4-methyl-3-salicylideneamino-1-(3-trifluoromethylphenyl)-2-pyrazoline;
3-benzylideneamino-1-(4-methoxyphenyl)-2-pyrazoline;
3-benzylideneamino-1-(3-carboxylphenyl)-2-pyrazoline;
3-(2-hydroxy-1-naphthylmethyleneamino)-1-(3-trifluoromethylphenyl)-2-pyrazoline;
1-(2-chlorophenyl)-3-(2-hydroxy-1-naphthylmethyleneamino)-2-pyrazoline.

The compounds of formula (I) may be prepared by any method known in the art for the preparation of compounds of analogous structure, for example, by the method of G. F. Duffin and J. D. Kendall in J. Chem. Soc. (1954), 408–415.

The compounds of formula (I) may be used in the relief of rheumatoid arthritis, rheumatoid spondylitis, osteroarthritis, gouty arthritis and other arthritic conditions; inflamed joints; eczema, other inflammatory skin conditions; inflammatory eye conditions including conjunctivitis; pyresis and other conditions associated with inflammation and pain. Such other conditions associated with inflammation include the reduction of tissue necrosis in chronic inflammation, the suppression of tissue rejection following transplant surgery and ulcerative colitis.

The compounds of formula (I) may also be used in the treatment or prophylaxis of allergic conditions and other airway inflammatory conditions such as asthma and of asthma having a non-allergic origin and bronchitis. The compounds may also be useful as antispasmogenic agents.

The amount required of a compound of formula (I) (herinafter referred to as the active ingredient) for therapeutic effect will, of course, vary both with the particular compound, the route of administration and the mammal under treatment. A suitable dose of a compound of formula (I) for a mammal suffering from an inflammatory, painful or pyretic condition as defined hereinbefore is 0.5 to 500 mg of base per kilogram bodyweight, the most preferred dosage being 0.5 to 50 mg/kg of mammal bodyweight, for example 5 to 25 mg/kg; administered two or three times daily.

In the case of the treatment or prophylaxis of inflammatory airway conditions, a suitable anti-asthmatic dose of a compound of formula (I) is 1 mg to 10 mg of base per kilogram bodyweight, the most preferred dosage being 1 mg to 5 mg/kg of mammal bodyweight, for example from 1 to 2 mg/kg.

While it is possible for an active ingredient to be administered alone as the raw chemical, it is preferable to present it as a pharmaceutical formulation. Conveniently, the active ingredient comprises from 0.1% to 99.9% by weight of the formulation. Conveniently, unit doses of a formulation contain between 0.1 mg and 1 g of the active ingredient. For topical administration, the active ingredient preferably comprises from 1% to 2% by weight of the formulation but the active ingredient may comprise as much as 10% w/w. Formulations suitable for nasal or buccal administration, (such self-propelling powder-dispensing formulations described hereinafter), may comprise 0.1 to 20% w/w, for example about 2% w/w of active ingredient.

The formulations, both for veterinary and for human medical use, of the present invention comprise an active ingredient in association with a pharmaceutically acceptable carrier therefor and optionally other therapeutic ingredient(s). The carrier(s) must be 'acceptable' in the sense of being compatible with the other ingredients of the formulations and not deleterious to the recipient thereof.

The formulations include those in a form suitable for oral, ophthalmic, rectal, parenteral (including subcutaneous, intramuscular and intravenous), intra-articular, topical, nasal or buccal administration.

The formulations may conveniently be presented in unit dosage form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units such as capsules, cachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be in the form of a bolus, electuary or paste.

A tablet may be made by compressing or moulding the active ingredient optionally with one or more accessory ingredients. Compressed tablets may be prepared by compressing, in a suitable machine, the active ingredient in a free-flowing form such as a powder or granules, optionally mixed with a binder, lubricant, inert diluent, surface active or dispersing agent. Moulded tablets may be made by moulding, in a suitable machine, a mixture of the powdered active ingredient and a suitable carrier moistened with an inert diluent.

Formulations for rectal administration may be in the form of a suppository incorporating the active ingredient and a carrier such as cocoa butter, or in the form of an enema.

Formulations suitable for parenteral administration conveniently comprise a sterile aqueous preparation of the active ingredient which is preferably isotonic with the blood of the recipient.

Formulations suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra-articular and ophthalmic administration.

Formulations suitable for topical administration include liquid or semi-liquid preparations such as liniments, lotions, applications; oil-in-water or water-in-oil emulsions such as creams, ointments or pastes; or solutions or suspensions such as drops. For example, for ophthalmic administration, the active ingredient may be presented in the form of aqueous eye drops as, for example, a 0.1–1.0% solution.

Formulations suitable for administration to the nose or buccal cavity include powder, self-propelling and spray formulations such as aerosols and atomizers. The formulations, when dispersed, preferably have a particle size in the range of 10 to 200u.

Such formulations are most preferably in the form of a finely comminuted powder for pulmonary administration from a powder inhalation device or self-propelling pwder-dispensing formulations, where the active ingredient, as a finely comminuted powder, may comprise up to 99.9% w/w of the formulation. In the case of self-propelling solution and spray formulations, the effect may be achieved either by choice of a valve having the desired spray characteristics (i.e. being capable of producing a spray having the desired particle size) or by incorporating the active ingredient as a suspended powder if controlled particle size. Thus the formulation, instead of passing into the lungs, is largely retained in the nasal cavity. These self-propelling formulations may be either powder-dispensing formulations or formulations dispensing the active ingredient as droplets of a solution or suspension.

Self-propelling powder-dispensing formulations preferably comprise dispersed particles of solid active ingredient, and a liquid propellant having a boiling point if below 65° F. (18° C.) at atmospheric pressure. The liquid propellant may be any propellant known to be suitable for medicinal administration and may comprise one or more lower alkyl hydrocarbons or halogenated lower alkyl hydrocarbons or mixtures thereof; chlorinated and fluorinated lower alkyl hydrocarbons are especially preferred. Generally, the propellant constitutes 50 to 99.9% w/w of the formulation whilst the active ingredient constitutes 0.1 to 20% w/w, for example, about 2% w/w, of the formulation.

The pharmaceutically acceptable carrier in such self-propelling formulations may include other constituents in addition to the propellant, in particular a surfactant or a solid diluent or both. Surfactants are desirable since they prevent agglomeration of the particles of active ingredient and maintain the active ingredient in suspension. Especially valuable are liquid non-ionic surfactants and solid anionic surfactants or mixtures thereof. Suitable liquid non-ionic surfactants are those having a hydrophile-lipophile balance (HLB, see Journal of the Society of Cosmetic Chemists Vol. 1 pp. 311–326 (1949)) of below 10, in particular esters and partial esters of fatty acids with alphatic polyhydric alcohols, for instance, sorbitan monooleate and sorbitan trioleate, known commercially as 'Span 80' (Trade Name) and 'Span 85' (Trade Name), respectively. The liquid non-ionic surfactant may constitute from 0.01 up to 20% w/w of the formulation, though preferably it constitutes below 1% w/w of the formulation. Suitable solid anionic surfactants include alkali metal, ammonium and amine salts of dialkyl sulphosuccinate (where the alkyl groups have 4 to 12 carbon atoms) and alkyl benzene sulphonic acid (where the alkyl group has 8 to 14 carbon atoms). The solid anionic surfactants may constitute from 0.01 up to 20% w/w of the formulation, though preferably below 1% w/w of the composition solid diluents may be advantageously incorporated in such self-propelling formulations where the density of the active ingredient differs substantially from the density of the propellant; also, they help to maintain the active ingredient in suspension. The solid diluent is in the form of a fine powder, preferably having a particle size of the same order as that of the particles of the active ingredient. Suitable solid diluents include sodium chloride, sodium sulphate and sugars.

Formulations of the present invention may also be in the form of a self-propelling formulation wherein the active ingredient is present in solution. Such self-propelling formulations may comprise the active ingredient, propellant and co-solvent, and advantageously an antioxidant stabiliser. The propellant is one or more of these already cited above. Co-solvents are chosen for their solubility in the propellant, their ability to dissolve the active ingredient, and for their having the lowest boiling point consistent with these above-mentioned properties. Suitable co-solvents are lower alkyl alcohols and mixtures thereof. The co-solvent may constitute 5 to 40% w/w of the formulation, though preferably less than 20% w/w of the formulation. Antioxidant stabilisers may be incorporated in such solution-formulations to inhibit deterioration of the active ingredient and are conveniently alkali metal ascorbates or bisulphites. They are preferably present in an amount of up to 0.25% w/w of the formulation.

Such self-propelling formulations may be prepared by any method known in the art. For example, the active ingredient (either as particles as defined hereinbefore in suspension in a suitable liquid or in up to 20% w/w solution in an acceptable co-solvent, as appropriate) is mixed with any other constituents of a pharmaceutically acceptable carrier. The resulting mixture is cooled, introduced into a suitable cooled container and propellant is added thereto in liquid form; and the container is sealed. Alternatively, such self-propelling formulations may be prepared by mixing the active ingredient either in particles as hereinbefore defined or in 2 to 20% w/v alcohol or aqueous solution as appropriate, together with the remaining constituents of the pharmaceutically acceptable carrier other than the propellant; introducing the resulting mixture, optionally with some propellant, into a suitable container; and injecting the propellant, under pressure, into the container at ambient temperature through a valve which comprises a part of the container and is used to control release of the formulation from it. Desirably, the container is purged by removing air from it at a convenient stage in the preparation of the self-propelling formulation.

A suitable container for a self-propelling formulation is one provided with a manually-operable valve and constructed of aluminium, stainless steel or reinforced glass. The valve should, of course, be one having the desired spray characteristics of particle size as hereinbefore defined. Advantageously, the valve is of the type which delivers a fixed amount of the formulation on the occasion of each operation of the valve, for example, about 50 to 100 microliters of formulation in each delivery.

Formulations of the present invention may also be in the form of an aqueous or dilute alcoholic solution, optionally a sterile solution, of the active ingredient for use in a nebuliser or atomiser, wherein an accelerated air stream is used to produce a fine mist consisting of small droplets of the solution. Such formulations usually contain a flavouring agent such as saccharin sodium and a volatile oil. A buffering agent such as sodium metabisulphite and a surface active agent may also be included in such a formulation which should also contain a preservative such as methylhydroxybenzoate.

Other formulations suitable for nasal administration include a coarse powder having a particle size of 20 to 500 microns which is administered in the manner if which snuff is taken i.e. by rapid inhalation through the nasal pasage from a container of the powder held close up to the nose.

In addition to the aforementioned ingredients, the formulations of this invention may include one or more additional ingredients such as diluents, buffers, flavouring agents, binder, surface active agents, thickeners, lubricants, preservatives eg. methylhydroxybenzoate (including anti-oxidants), emulsifying agents and the like.

Any other therapeutic ingredient may comprise one or more of the following: anti-biotic, anti-fungal and anti-viral agents.

According to the present invention there are therefore provided:

(a) a novel compound of formula (I) or an acid addition salt thereof;

(b) a method for preparing a compound of formula (I);

(c) a pharmaceutical formulation comprising a non-toxic, effective arachidonic acid oxygenation inhibitory amount of a compound of formula (I) or a pharmaceutically acceptable salt thereof and a pharmaceutically acceptable carrier therefor;

(d) a method for preparing such formulations;

(e) a method for the prophylaxis or treatment of inflammation in a mammal, including man, comprising the administration to said mammal of a non-toxic, effective anti-inflammatory amount of a compound of formula (I);

(f) a method for the prophylaxis or treatment of pain in a mammal, including man, comprising the administration to said mammal of a non-toxic, effective analgesic amount of a compound of formula (I);

(g) a method for the prophylaxis or treatment of pyresis in a mammal, including man, comprising the administration to said mammal of a non-toxic, effective anti-pyretic amount of a compound for formula (I);

(h) a method for the prophylaxis or treatment of asthma in a mammal, including man, comprising the administration to said mammal of a non-toxic, effective, anti-asthmatic amount of a compound of formula (I);

(i) a method for the inhibition of a pathway of arachidonic acid oxygenation selected from the lipoxygenase and cyclo-oxygenase pathways, comprising the administration of a non-toxic, effective, inhibitory amount of a compound of formula (I) or a pharmaceutically acceptable acid addition salt thereof; and (j) a compound of formula (I) for use in medicine in the inhibition of the lipoxygenase or cyclo-oxygenase pathways of arachidonic acid metabolism.

The following examples are provided by way of an illustration of the present invention and should in no way be construed as a limitation thereof. All temperatures indicated are in degrees Celsius.

EXAMPLE 1

Preparation of 3-(2,4'-carboxybutoxy-6-hydroxybenzylidine-amino)-1-(3-trifluoromethylphenyl)-2-pyrazoline 3-Amino-1-(3-trifluoromethylphenyl)-2-pyrazoline (438 mg) in methanol (4 ml) was mixed together with 2-4'-carboxybutoxy-6-hydroxybenzaldehyde (476 mg). A deep orange rapidly developed. The mixture was heated to reflux for 1½ hours during which time the reaction mixture set to a semi-solid mass. The mixture was cooled to 0° and the solid filtered off, washed with fresh methanol and dried in vacuo to produce 3-(2-4'-carboxybutoxy-6-hydroxybenzylideneamino)-1-(3-trifluoromethylphenyl)-2-pyrazoline, m.p. 179.1°.
Analysis: Required: C, 58.79; H, 4.93; N, 9.35; Found: C, 58.98; H, 5.00; N, 9.19.

EXAMPLE 2

Preparation of 3-(2-pyridylmethyleneamino)-1-(3-trifluoromethylphenyl)-2-pyrazoline 3-Amino-1-(3-trifluoromethylphenyl)-2-pyrazoline in methanol (23 ml) was stirred together with 2-pyridylaldehyde at room temperature for 2 hours and then under reflux for a further 2 hours. Thin layer chromatography ($SiO_2$, ethyl acetate) indicated that the reaction was substantially complete. After standing overnight, additional 2-pyridylaldehyde (0.5 g) was added and heating was continued for 2 hours. TLC again indicated that no further reaction had occurred. The reaction mixture was evaporated in vacuo to yield an orange-coloured solid which was stirred for 45 minutes in aqueous ethanol (3:1) and 3-(2-pyridylmethyleneamino)-1-(3-trifluoromethylphenyl)-2-pyrazoline was collected, m.p. 155.6°.
Analysis: $C_{16}H_{13}F_3N_4$; Required: C, 60.38; H, 4.11; N, 17.60; Found: C, 60.29; H, 4.18; N, 17.58.

EXAMPLE 3

Preparation of 3-(2-pyrrolylmethyleneamino)-1-(3-trifluoromethylphenyl)-2-pyrazoline 3-Amino-1-(3-trifluoromethylphenyl)-2-pyrazoline (0.6 g) in n-butanol (4 ml) was heated together with 2-pyrroylaldehyde (0.25 g) to 100° overnight under a nitrogen atmosphere. TLC (see example 1) indicated that a partial reaction had occurred. Heating was continued for a further 24 hours after which time little further reaction had occurred. The reaction mixture was left at room temperature under a nitrogen atmosphere for 4 days during which time dark-coloured crystals had formed which were collected and re-crystallized from aqueous isopropanol. The product was 3-(2-pyrrolylmethyleneamino)-1-(3-trifluoromethylphenyl)-2-pyrazoline, m.p. 144°–145°.
Analysis: $C_{15}H_{13}F_3N_4$; Required: C, 58.82; H, 4.28; N, 18.29; Found: C, 59.04; H, 4.20; N, 18.5.

EXAMPLE 4

Preparation of 3-salicylidenamino-1-(3-trifluoromethylphenyl)-2-pyrazoline

A. A solution of 3-amino-1-(3-trifluoromethylphenyl)-2-pyrazoline (2.29 g) and salicylaldehyde (1.2 g) in methanol (22.9 ml) was heated to reflux for 30 minutes. The resulting semi-solid mass was cooled and then filtered to give an orange-coloured solid which was re-crystallized from ethanol to produce 3-salicylideneamino-1-(3-trifluoromethylphenyl)-2-pyrazoline m.p. 159.1° (yield 1.7 g).
Analysis: $C_{17}H_{14}F_3N_3O$; Required: C, 61.3; H, 4.1; N, 12.6; Found: C, 61.06; H, 4.36; N, 12.11.

B. Salicylaldehyde (80 mg) was added to a solution of 3-amino-1-(3-trifluoromethylphenyl)-2-pyrazoline hydrochloride (130 mg) in water (5 ml). The salicylaldehyde layer rapidly turned orange and after about 10 minutes a semi-solid mass had formed. Ethanol (1 ml) was added to give a clear solid. The mixture was kept overnight at room temperature and the product was collected and washed with water containing 5% ethanol and finally, dried in vacuo to produce 3-salicylideneamino-1-(3-trifluoromethylphenyl)-2-pyrazoline, m.p. 155.8° (yield 130 mg). The product was then re-crystallized with ethanol and on subsequent analysis, was found to be identical with that described in paragraph A.

EXAMPLE 5

Preparation of 3-salicylideneamino-1-(2-pyridyl)-2-pyrazoline

3-Amino-1-(2-pyridyl)-2-pyrazoline (1.6 g) and salicylaldehyde (1.2 g) were dissolved together with methanol (16 ml). The resulting solution was heated to reflux and after about 15 minutes a crystalline solid separated. After another 15 minutes at reflux the suspension was cooled and the separated 3-salicylideneamino-1-(2-pyridyl)-2-pyrazoline was recrystallized from methanol m.p. 242°–243° (yield 500 mg).

Analysis: $C_{15}H_{14}N_4O$; Required: C, 67.65; H, 5.3; N, 21.04; Found: C, 67.60; H, 5.34; N, 21.38.

EXAMPLE 6

Preparation of
3-(3-quinolylmethyleneamino)-1-(3-trifluoromethylphenyl)-2-pyrazoline A mixture of 3-amino-1-(3-trifluoromethylphenyl)-2-pyrazoline (prepared in Reference Example 1 of our European patent specification No. 22-578) (0.73 g), 3-quinoline carboxaldehyde (0.5 g) and 1 drop glacial acetic acid in methanol (10 ml) was heated to reflux for thirty minutes. After cooling, the solid product was collected and recrystallized from ethanol, and subsequently from ethyl acetate and from toluene to afford 3-(3-quinolymethyleneamino)-1-(3-trifluoromethylphenyl)-2-pyrazoline, m.p. 209°–210°.

EXAMPLE 7

Preparation of
3-(1-naphthylmethyleneamino)-1-(3-trifluoromethylphenyl)-2-pyrazoline A solution of 3-amino-1-(3-trifluoromethylphenyl)-2-pyrazoline (prepared in Reference Example 1 of our European patent specification No. 22-578) (10 g) and 1-naphthaldehyde (6.81 g) containing four drops of glacial acetic acid was heated to reflux in ethanol (50 ml) for twenty four hours. The resultant solid was collected and recrystallized from propan-1-ol to yield 3-(1-naphthylmethyleneamino)-1-(3-trifluoromethylphenyl)-2-pyrazoline, m.p.173°.

EXAMPLE 8

Preparation of
3-(4-methylbenzylideneamino)-1-(2-naphthyl)-2-pyrazoline

Example 8A: 3-amino-1-(2-naphthyl)-2-pyrazoline

2-Hydrazinonaphthalene (5 g) was added to a solution of sodium (0.7 g) in dried S.V.M. (20 ml) in a nitrogen atmosphere at 0°–5°. Acrylonitrile (1.8 g) was then added slowly and the resulting mixture allowed to attain room temperature over about 1 hour.

The mixture was then heated to reflux; after about 30 minutes it deposited a crystalline solid and after about 45 minutes a semi-solid mass had formed. After a total heating time of 1 hour, the mixture was allowed to cool and the solid filtered off with care.

The filtrate was deep purple but the residue was a clear yellow solid which was ground up with water, filtered and re-ground with S.V.M. After further filtering and grinding with S.V.M., the product was finally filtered, washed with S.V.M. and dried in vacuo to yield 4.4 g of 3-amino-1-(2-naphthyl)-2-pyrazoline, m.p. 190°–191°.

EXAMPLE 8B:
3-(4-methylbenzylideneamino)-1-(2-naphthyl)-2-pyrazoline

The amino compound prepared in Example 8A (500 mg) was suspended in S.V.M. (25 ml) together with 4-methylbenzaldehyde (300 mg) and 1 drop of glacial acetic acid. The mixture was stirred at reflux temperature for 2 hours. A dark orange solid formed and the reaction mixture was cooled and filtered to produce a dark yellow solid.

The product was washed with methanol and dried in vacuo to give 3-(4-methylbenzylideneamino)-1-(2-naphthyl)-2-pyrazoline, m.p. 184°–186°.

EXAMPLE 9

Preparation of
3-salicylideneamino-1-(3-quinolyl)-2-pyrazoline

3-Amino-1-(3-quinolyl)-2-pyrazoline (prepared in Example 10 of our co-pending application No. (A629)) (1.06 g, 0.005 mol) was added to a solution of salicylaldehyde (0.61 g, 0.005 mol) in methanol (8 ml). The mixture was refluxed for ½ hour and then the solid filtered off.

The solid was refluxed in methanol (200 ml) for ½ hour, the insoluble material filtered off and the product recrystallized from 2-ethoxyethanol with charcoaling to yield 0.14 g 3-salicylideneamino-1-(3-quinolyl)-2-pyrazoline, m.p. 288°–289°.

EXAMPLE 10

Preparation of
3-(4-chlorobenzylideneamino)-1-(4-chlorophenyl)-2-pyrazoline

3-Amino-1-(4-chlorophenyl)-2-pyrazoline (prepared in Reference Example 6 of our European patent specification No. 22-578) (1.95 g) in S.V.M. (5 ml) was mixed with excess 4-chlorobenzaldehyde (1.50 g) and the mixture was heated to reflux after the addition of 1 drop of glacial acetic acid. A virtually clear solution formed which rapidly crystallised to form a bright orange product which was collected, washed with S.V.M. and dried in vacuo to produce 2.95 g 3-(4-chlorobenzylideneamino)-1-(4-chlorophenyl)-2-pyrazoline, m.p. 193°–195° (decomp).

EXAMPLE 11

Preparation of
1-(4-bromo-3-trifluoromethylphenyl)-3-(2-hydroxybenzylideneamino)-2-pyrazoline 3-Amino-1-(4-bromo-3-trifluoromethylphenyl)-2-pyrazoline (prepared in Example 39 of our European patent specification No. 22-578) (140 mg) and salicylaldehyde (100 mg) were dissolved together in methanol (2 ml) and 1 drop of glacial acetic acid. The mixture was heated to reflux for 1 hour. During this time a deep orange-red colour developed and the mixture crystallised. It was kept at 0° for 3 hours, then the solid was collected, washed with methanol and dried in vacuo to yield 150 mg 1-(4-bromo-3-trifluoromethylphenyl)-3-(2-hydroxybenzylideneamino)-2-pyrazoline, m.p. 170° (decomp).

EXAMPLE 12

Preparation of
1-(4-bromo-3-trifluoromethylphenyl)-3-(4-methoxybenzylideneamino)-2-pyrazoline 3-Amino-1-(4-bromo-3-trifluoromethylphenyl)-2-pyrazoline (prepared in Example 39 of our European patent specification No. 22-578) (240 mg) in S.V.M. (5 ml) together with 4-methoxybenzaldehyde (160 mg) and 1 drop of glacial acetic acid were heated to reflux for 1 hour. A yellow product separated which was collected, washed with methanol and dried in vacuo to yield 300 mg 1-(4-bromo-3-trifluoromethylphenyl)-3-(4- methoxybenzylideneamino)-2-pyrazoline, m.p. 175°–176° (decomp).

EXAMPLE 13

3-Amino-1-(3-t-butylphenyl)-2-pyrazoline 3-t-Butylaniline hydrochloride (5 g) in concentrated hydrochloric acid (8 ml) was stirred at 0° whilst a solution of sodium nitrite (1.86 g) in water (2.4 ml) was slowly added. The mixture was kept at 0° for 1 hour and, after filtering (at 0°), it was treated dropwise with a solution of stannous chloride dihydrate (18.2 g) in concentrated hydrochloric acid (18.8 ml). A pink-coloured solid separated. After 1 hour, this solid was filtered off and washed with saturated aqueous sodium chloride. The resulting salt was converted into base in the usual way to give 3-t-butylphenylhydrazine, b.p. 88°–90°/0.25 mm Hg.

This hydrazine (1.2 g) was then added to a solution of sodium (0.029 g) in ethanol (1.5 ml) at room temperature in an atmosphere of nitrogen. The resulting solution was cooled to −10°, acrylonitrile (0.24 ml) added and the mixture heated to reflux for 5 hours. The solid which separated on cooling was recrystallized from light petroleum (b.p. 80°–100°) to give 3-amino-1-(t-butylphenyl)-2-pyrazoline, m.p. 113.5° (yield 648 mg).

EXAMPLE 14

3-benzylideneamino-1-(3-t-butylphenyl)-2-pyrazoline

3-Amino-1-(3-t-butylphenyl)-2-pyrazoline (500 mg) was reacted with benzaldehyde (500 mg) in boiling methanol (5 ml) in the presence of glacial acetic acid (1 drop). After some 4 hours, the mixture was cooled and 3-benzylideneamino-1-(3-t-butylphenyl)-2-pyrazoline separated in crystals m.p. 140°–141°, (yield 500 mg).

EXAMPLES 15 to 22

By a method analogous to that described in detail in the foregoing Examples were also prepared the following:

EXAMPLE 15

3-Benzylideneamino-1-(3-trifluoromethylphenyl)-2-pyrazoline, m.p. 162°–163°.

EXAMPLE 16

1-(5-Bromo-6-methyl-2-pyridyl)-3-salicylideneamino-2-pyrazoline, m.p. 215°–216°.

EXAMPLE 17

1-(5-Bromo-6-methyl-2-pyridyl)-3-(1-naphthylmethyleneamino)-2-pyrazoline, m.p. 199°.

EXAMPLE 18

4-Methyl-3-salicylideneamino-1-(3-trifluoromethylphenyl)-2-pyrazoline, m.p. 105°–106°.

EXAMPLE 19

3-Benzylideneamino-1-(4-methoxyphenyl)-2-pyrazoline, m.p. 199°–200°.

EXAMPLE 20

3-Benzylideneamino-1-(3-carboxylphenyl)-2-pyrazoline

3-Amino-1-(3-carboxyphenyl)-2-pyrazoline (850 mg) in methanol (10 ml) was treated with benzaldehyde (870 mg) and glacial acetic acid (1 drop). The mixture was heated to reflux for 7 hours, then left to cool overnight.

The resultant product was filtered off and recrystallised from n-propanol to yield 3-benzylideneamino-1-(3-carboxyphenyl)-2-pyrazoline, m.p. 185°.

EXAMPLE 21

3-(2-Hydroxy-1-naphthylmethyleneamino)-1-(3-trifluoromethylphenyl)-2-pyrazoline, m.p. 247°–249°.

EXAMPLE 22

1-(2-Chlorophenyl)-3-(2-hydroxy-1-naphthylmethyleneamino)-2-pyrazoline, m.p. 195°–197°.

EXAMPLE A

Tablet

| In one tablet | |
|---|---|
| Active Ingredient | 5.0 mg |
| Lactose | 82.0 mg |
| Starch | 10.0 mg |
| Povidone | 2.0 mg |
| Magnesium stearate | 1.0 mg |

Mix together the active ingredient, lactose and starch. Granulate the powders using a solution of povidone in purified water. Dry the granules, add the magnesium stearate and compress to produce tablets, 100 mg per tablet.

EXAMPLE B

Ointment

| Active Ingredient | 1.0 g |
|---|---|
| White soft paraffin to | 100.0 g |

Disperse the active ingredient in a small volume of the vehicle. Gradually incorporate this into the bulk to produce a smooth, homogeneous product. Fill into collapsible metal tubes.

EXAMPLE C

Cream for Topical Use

| Active Ingredient | 1.0 g |
|---|---|
| Polawax GP 200 | 20.0 g |
| Lanolin Anhydrous | 2.0 g |
| White Beeswax | 2.5 g |
| Methyl Hydroxybenzoate | 0.1 g |
| Distilled Water to | 100.0 g |

Heat the polawax, beeswax and lanolin together at 60°. Add a solution of methyl hydroxybenzoate. Homogenise using high speed stirring. Allow the temperature to fall to 50°. Add and disperse the active ingredient. Allow to cool with slow speed stirring.

EXAMPLE D

Lotion for Topical Use

| Active Ingredient | 1.0 g |
|---|---|
| Sorbitan Monolaurate | 0.6 g |
| Polysorbate 20 | 0.6 g |
| Cetostearyl Alcohol | 1.2 g |
| Glycerin | 6.0 g |
| Methyl Hydroxybenzoate | 0.2 g |
| Purified Water to | 100.0 ml |

The methyl hydroxybenzoate and glycerin were dissolved in 70 ml of the water at 75° C. The sorbitan monolaurate, polysorbate 20 and cetostearyl alcohol were melted together at 75° and added to the aqueous solution. The resulting emulsion was homogenised, allowed to cool with continuous stirring and the active ingredient added as a suspension in the remaining water. The whole was stirred until homogenous.

EXAMPLE E

Eye Drops

| | |
|---|---|
| Active Ingredient | 0.5 g |
| Methyl Hydroxybenzoate | 0.01 g |
| Propyl Hydroxybenzoate | 0.04 g |
| Purified Water B.P. to | 100.00 ml |

The methyl and propyl hydroxybenzoates were dissolved in 70 ml purified water at 75° and the resulting solution then allowed to cool. The active ingredient was added next and the solution made up to 100 ml with purified water. The solution was sterilised by filtration through a membrane filter 0.22 um pore size and packed aseptically into suitable sterile containers.

EXAMPLE F

Injection Solution

| | |
|---|---|
| Active Ingredient | 10.0 mg |
| Water for Injections B.P. | 1.0 ml |

The active ingredient was dissolved in half of the Water for Injections and then made up to volume and sterilised by filtration. The resulting solution was distributed into ampoules under aseptic conditions.

EXAMPLE G

Inhibition of Lipoxygenase and Cyclo-oxygenase

In an enzyme assay according to the method of G. Blackwell and R. J. Flower (Br.J.Pharmac., 63: 360(1978)), compounds of the invention were found to have an $IC_{50}$ (uM) for inhibition of each of lipoxygenase and cyclo-oxygenase as indicated in Table I:

TABLE I

| | $IC_{50}$ (μM) | |
|---|---|---|
| Compound | Cyclo-oxygenase | Lipoxygenase |
| of Example 1 | <3 | 10-20 |
| of Example 2 | 1 | ~3 |
| of Example 3 | <1 | 1 |
| of Example 4 | ~3 | ~3 |
| of Example 7 | 10 | 6 |
| of Example 8 | 5 | 12 |
| of Example 11 | ~5 | >10 |
| of Example 12 | ~1 | ~1 |
| of Example 13 | <1 | <1 |
| of Example 15 | ~3 | <1 |
| of Example 18 | ~1 | ~1 |

What we claim is:

1. 3-Salicylideneamino-1-(3-trifluoromethylphenyl)-2-pyrazoline.

2. A pharmaceutical formulation useful in treating inflammation in mammals comprising an effective amount of a compound of formula (I) or a pharmaceutically acceptable salt thereof:

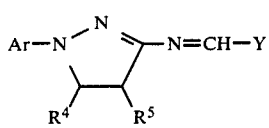

wherein, Y is a monocyclic or bicyclic aromatic radical selected from phenyl, naphthyl, quinolyl, and pyridyl optionally substituted in any position of the ring by one or more substituent(s) selected from fluoro, chloro, bromo or iodo, nitro, carboxy, hydroxy, amino, monoalkyl substituted-amino, dialkyl substituted-amino, monohalo substituted-alkyl, dihalo substituted-alkyl, trihalo substituted-alkyl, alkyl, alkoxy, carboxyalkoxy, alkylsulphonyl, monohalo substituted-alkyl sulphonyl, dihalo substituted-alkyl sulphonyl and trihalo substituted-alkyl sulphonyl; $R^4$ and $R^5$ are each the same or different and are each selected from hydrogen, alkyl, or Y as defined above; and Ar is selected from Y as defined above with the proviso that Ar is other than unsubstituted phenyl.

3. A formulation according to claim 2 in which the compound or a pharmaceutically acceptable salt thereof is of formula (IA):

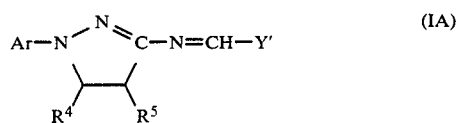

wherein, Y is phenyl, pyridyl, naphthyl or quinolyl, each of which may optionally be substituted by one or more of halo, alkyl, alkoxy and hydroxy groups; $R^4$ and $R^5$ are the same or different and are each selected from hydrogen and alkyl; and Ar is pyridyl, quinolyl or substituted-phenyl, each of which pyridyl and quinolyl may be optionally substituted by one or more substituents, and the substituents are selected from halo, alkyl (which may itself be optionally substituted by halo), alkoxy and carboxyl groups.

4. A pharmaceutical formulation useful in treating inflammation in humans comprising an effective amount of a compound selected from:
3-salicylideneamino-1-(3-trifluoromethylphenyl)-2-pyrazoline;
3-benzylideneamino-1-(3-trifluoromethylphenyl)-2-pyrazoline;
3-(2,4-dihydroxybenzylideneamino)-1-(3-trifluoromethylphenyl)-2-pyrazoline;
3-(2-pyridylmethyleneamino)-1-(3-trifluoromethylphenyl)-2-pyrazoline;
3-salicylideneamino-1-(2-pyridyl)-2-pyrazoline;
3-(3-quinolylmethyleneamino)-1-(3-trifluoromethylphenyl)-2-pyrazoline;
3-(1-naphthylmethyleneamino)-1-(3-trifluoromethylphenyl)2-pyrazoline;
3-(4-methylbenzylideneamino)-1-(2-naphthyl)-2-pyrazoline;
3-salicylideneamino-1-(3-quinolyl)-2-pyrazoline;
3-(4-chlorobenzylideneamino)-1-(4-chlorophenyl)-2-pyrazoline;
3-(2-hydroxybenzylideneamino)-1-(4-bromo-3-trifluoromethylphenyl)-2-pyrazoline;
3-(4-methoxybenzylideneamino)-1-(4-bromo-3-trifluoromethylphenyl)-2-pyrazoline;
3-benzylideneamino-1-(3-t-butylphenyl)-2-pyrazoline;

3-salicylideneamino-1-(5-bromo-6-methyl-2-pyridyl)-2-pyrazoline;
3-(1-naphthylmethyleneamino)-1-(5-bromo-6-methyl-2-pyridyl)-2-pyrazoline;
4-methyl-3-salicylideneamino-1-(3-trifluoromethylphenyl)-2-pyrazoline;
3-benzylideneamino-1-(4-methoxyphenyl)-2-pyrazoline;
3-benzylideneamino-1-(3-carboxyphenyl)-2-pyrazoline;
3-(2-hydroxy-1-naphthylmethyleneamino)-1-(3-trifluoromethylphenyl)-2-pyrazoline;
3-(2-hydroxy-1-naphthylmethyleneamino)-1-(2-chlorophenyl)-2-pyrazoline or a pharmaceutically acceptable salt thereof.

5. A formulation according to claim 2 in unit dosage form.

6. A formulation according to claim 2 in the form of capsules, tablets, suppositories, liniments, lotions, creams ointments, drops or aerosols.

7. A formulation according to claim 2 in a form suitable for ophthalmic administration.

8. A formulation according to claim 2 in the form of aqueous eye drops.

9. A formulation according to claim 2, wherein the compound or salt of formula (I) is further in association with another therapeutic ingredient selected from antibiotic, anti-fungal and anti-viral agents.

10. A pharmaceutical formulation useful in treating inflammation in mammals comprising an effective amount of 3-salicylideneamino-1-(3-trifluoromethylphenyl)-2-pyrazoline or a pharmaceutically acceptable salt thereof.

11. A method for prophylaxis or treatment of inflammation in a mammal in need thereof, including man, comprising the administration to said mammal of a non-toxic, effective anti-inflammatory amount of a compound of formula (I) or a pharmaceutically acceptable salt thereof:

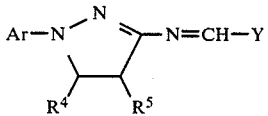

wherein, Y is a monocyclic or bicyclic aromatic radical selected from phenyl, naphthyl, quinolyl, and pyridyl optionally substituted in any position of the ring by one or more substituent(s) selected from fluoro, chloro, bromo or iodo, nitro, carboxy, hydroxy, amino, monoalkyl substituted-amino, dialkyl substituted-amino, monohalo substituted-alkyl, dihalo substituted-alkyl, trihalo substituted-alkyl, alkyl, alkoxy, carboxyalkoxy, alkylsulphonyl, monohalo substituted-alkyl sulphonyl, dihalo substituted-alkyl sulphonyl and trihalo substituted-alkyl sulphonyl; $R^4$ and $R^5$ are each the same or different and are each selected from hydrogen, alkyl, or Y as defined above; and Ar is selected from Y as defined above with the proviso that Ar is other than unsubstituted phenyl.

12. A method for the prevention or treatment of inflammation in a mammal in need thereof comprising the administration to said mammal of 3-salicylideneamino-1-(3-trifluoromethylphenyl)-2-pyrazoline or a pharmaceutically acceptable salt thereof.

13. The method of claim 12 in which the mammal is a human.

14. A method for the prophylaxis or treatment of pain in a mammal in need thereof, including man, comprising the administration to said mammal of a non-toxic, effective analgesic amount of a compound of formula (1) or a pharmaceutically acceptable salt thereof:

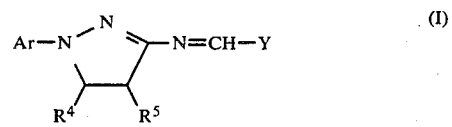

wherein, Y is a monocyclic or bicyclic aromatic radical selected from phenyl, naphthyl, quinolyl, and pyridyl optionally substituted in any position of the ring by one or more substituent(s) selected from fluoro, chloro, bromo or iodo, nitro, carboxy, hydroxy, amino, monoalkyl substituted-amino, dialkyl substituted-amino, monohalo substituted-alkyl, dihalo substituted-alkyl, trihalo substituted-alkyl, alkyl, alkoxy, carboxyalkoxy, alkylsulphonyl, monohalo substituted-alkyl sulphonyl, dihalo substituted-alkyl sulphonyl and trihalo substituted-alkyl sulphonyl; $R_4$ and $R^5$ are each the same or different and are each selected from hydrogen, alkyl, or Y as defined above; and Ar is selected from Y as defined above with the proviso that Ar is other than unsubstituted phenyl.

15. A method of inhibiting the lipoxygenase or cyclooxygenase pathways of arachidonic acid metabolism in a mammal in need thereof comprising the administration of an effective inhibitory amount of a compound of formula (I) or a pharmaceutically acceptable salt thereof:

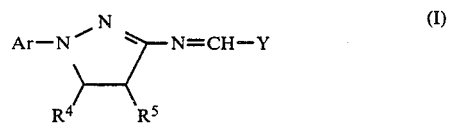

wherein, Y is a monocyclic or bicyclic aromatic radical selected from phenyl, naphthyl, quinolyl, and pyridyl optionally substituted in any position of the ring by one or more substituent(s) selected from fluoro, chloro, bromo or iodo, nitro, carboxy, hydroxy, amino, monoalkyl substituted-amino, dialkyl substituted-amino, monohalo substituted-alkyl, dihalo substituted-alkyl, trihalo substituted-alkyl, alkyl, alkoxy, carboxyalkoxy, alkylsulphonyl, monohalo substituted-alkyl sulphonyl, dihalo-substituted-alkyl sulphonyl and trihalo substituted-alkyl sulphonyl; $R_4$ and $R_5$ are each the same or different and are each selected from hydrogen, alkyl, or Y as defined above; and Ar is selected from Y as defined above with the proviso that Ar is other than unsubstituted phenyl.

16. A method for the prophylaxis or treatment of pyresis in a mammal in need thereof, including man comprising the administration to said mammal of an effective amount of a compound of formula (I) or a pharmaceutically acceptable salt thereof:

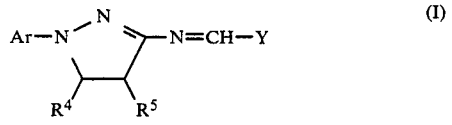

wherein, Y is a monocyclic or bicyclic aromatic radical selected from phenyl, naphthyl, quinolyl, and pyridyl optionally substituted in any position of the ring by one or more substituent(s) selected from fluoro, chloro, bromo or iodo, nitro, carboxy, hydroxy, amino, monoalkyl substituted-amino, dialkyl substituted-amino, monohalo substituted-alkyl, dihalo substituted-alkyl, trihalo substituted-alkyl, alkyl, alkoxy, carboxyalkoxy, alkylsulphonyl, monohalo substituted-alkyl sulphonyl, dihalo substituted-alkyl sulphonyl and trihalo substituted-alkyl sulphonyl; $R^4$ and $R^5$ are each the same or different and are selected from hydrogen, alkyl, or Y as defined above; and Ar is selected from Y as defined above with the proviso that Ar is other than unsubstituted phenyl.

17. A method for the prophylaxis or treatment of asthma in a mammal in need thereof comprising the administration to a mammal of an antiasthmatic amount of a compound of formula (I) or a pharmaceutically acceptable salt thereof:

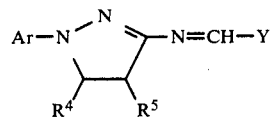

wherein, Y is a monocyclic or bicyclic aromatic radical selected from phenyl, naphthyl, quinolyl, and pyridyl optionally substituted in any position of the ring by one or more substituent(s) selected from fluoro, chloro, bromo or iodo, nitro, carboxy, hydroxy, amino, monoalkyl substituted-amino, dialkyl substituted-amino, monohalo substituted-alkyl, dihalo substituted-alkyl, trihalo substituted-alkyl, alkyl, alkoxy, carboxyalkoxy, alkylsulphonyl, monohalo substituted-alkyl sulphonyl, dihalo substituted-alkyl sulphonyl and trihalo substituted-alkyl sulphonyl; $R^4$ and $R^5$ are each of the same or different and are each selected from hydrogen, alkyl, or Y as defined above; and Ar is selected from Y as defined above with the proviso that Ar is other than unsubstituted phenyl.

* * * * *